(12) United States Patent
Lunney et al.

(10) Patent No.: US 6,770,440 B1
(45) Date of Patent: Aug. 3, 2004

(54) POLYMERASE CHAIN REACTION ASSAY FOR THE DETECTION OF *TOXOPLASMA GONDII*

(75) Inventors: Joan K. Lunney, Bethesda, MD (US); Luis H. Jauregui, Buenos Aires (AR); James Higgins, Laurel, MD (US); Dante S. Zarlenga, Ellicott City, MD (US); Jitender P. Dubey, Greenbelt, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/867,435

(22) Filed: May 31, 2001

(51) Int. Cl.[7] .......................... C12Q 1/68; C12P 19/34; C07H 21/02; C07H 21/04
(52) U.S. Cl. ........................ 435/6; 435/91.2; 536/23.1; 536/24.32; 536/24.33
(58) Field of Search ................... 435/6, 91.2; 536/23.1, 536/24.32, 24.33

(56) References Cited

U.S. PATENT DOCUMENTS

| | | | | |
|---|---|---|---|---|
| 5,688,644 A | * | 11/1997 | Lott et al. ....................... | 435/6 |
| 5,723,591 A | * | 3/1998 | Livak et al. ................ | 536/22.1 |

OTHER PUBLICATIONS

Payne et al. International Journal for Parasitology. 1996. 26: 347–351.*

Johnson, J.D., et al., "Detection of *Toxoplasma gondii* Using the Polymerase Chain Reaction", Abstract: *Transactions–Biochemical Society*, vol. 18(4), p. 665, Aug. 1990.

Jauregui, L.H., et al., "Evaluation of a Fluorogenic Real-Time PCR Assay for the Detection of *Toxoplasma gondii* in Biological Samples", Abstract: *Proceedings of the 81st Annual Meeting*, Nov. 12–14, 2000, The Congress Hotel, Chicago.

Ellis, J.T., "Polymerase Chain Reaction Approaches for the Detection of *Neospora caninum* and *Toxoplasma gondii*", *International J. for Parasitology*, vol. 28, pp. 1053–1060, 1998.

Guay, J.M., et al., "Detection of the Pathogenic Parasite *Toxoplasma gondii* by Specific Amplification of Ribosomal Sequences Using Comultiplex Polymerase Chain Reaction", *J. of Clinical Microbiology*, vol. 31(2), pp. 203–207, Feb. 1993.

Tenter, A.M., et al., "Species–Specific Indentification of Sarcocystis and Toxoplasma by PCR Amplification of Small Subunit Ribosomal RNA Gene Fragments", *Appl. Parasitol.*, vol. 35(3), pp. 173–188, 1994.

Warnekulasuriya, M.R., et al., "Detection of *Toxoplasma gondii* in Cured Meats", *International J. of Food Microbiology*, vol. 45, pp. 211–215, 1998.

Gamble, H.R., et al., "Detection of Parasites in Food", *Parasitology*, vol. 117, pp. S97–S111, 1998.

Voglino, G., et al., "Linfoadenopatia da Toxoplasma in Linfonodo Intramammario: Ruolo Della Biolgia Molecolare Nella Diagnosi", *Pathologica*, vol. 89, pp. 446–448, 1997.

Toth, T., et al., "PCR Detection of *Toxoplasma gondii* in Human Fetal Tissues", *Methods in Mol. Biol.*, vol. 92: *PCR in Bioanalysis*), pp. 195–202, 1998.

Sumathi, S., et al., "Nested PCR Assay for Direct Detection of *Toxoplasma Gondii* DNA in Serum and Blood Samples", *Biomed. Res.*, vol. 10(2), pp. 147–151, 1999.

Costa, J.M., et al., "Real–Time PCR for Diagnosis and Follow–Up of Toxoplasma Reactivation after Allogneic Stem Cell Transplantation Using Fluorescence Resonance Energy Transfer Hybridization Probes", *J. of Clinical Microbiology*, vol. 38(8), pp. 2929–2932, Aug. 2000.

Heid, C., et al., "Real Time Quantitative PCR", *Genome Research*, Chapter 6, pp. 986–994, 1996.

Howe, D., et al., "*Toxoplasma gondii* Comprises Three Clonal Lineages: Correlation of Parasite Genotype with Human Diseases", *J. Infectious Disease*, vol. 172, pp. 1561–6, Dec., 1995.

James, G., et al., "Comparison of Cell Culture, Mouse Inoculation, and PCR for Detection of *Toxoplasma gondii*: Effects of Storage Conditions on Sensitivity", *J. Clinical Microbiology*, vol. 34(6), pp. 1572–1575, Jun., 1996.

Dupon, M., et al., "Detection of *Toxoplasma gondii* by PCR and Tissue Culture in Cerebrospinal Fluid and Blood of Human Immunodeficiency Virus–Seropositive Patients", *J. Clinical Microbiology*, vol. 33(9), pp. 2421–2426, Sep. 1995.

Homan, W., et al., "Identification of a 200– to 300–Fold Repetitive 529 bp DNA Fragment in *Toxoplasma gondii*, and its Use for Diagnostic and Quantitative PCR", *International J. for Parasitology*, vol. 30, pp. 69–75, 2000.

Esteban–Redondo, I. et al., "Detection of *Toxoplasma gondii* in Tissues of Sheep Orally Challenged with Different Doses of Oocysts", *International J. for Parasitology*, vol. 28, pp. 1459–1466, 1998.

(List continued on next page.)

*Primary Examiner*—Carla J. Myers
(74) *Attorney, Agent, or Firm*—John D. Fado; Janelle S Graeter (57) ABSTRACT

Oligonucleotide primer sequences have been designed which are capable of uniquely amplifying DNA from *Toxoplasma gondii* when utilized in a polymerase chain reaction assay. In addition, a probe effective for detection of amplification products, particularly in a fluorogenic real time assay system has also been designed. The primers and probe are derived from the internal transcribed spacer 1 (ITS1) region of the *T. gondii* 18S rRNA gene.

22 Claims, 4 Drawing Sheets

OTHER PUBLICATIONS

Kaufmann, H., et al., "Discrimination of *Neospora caninum* from *Toxoplasma gondii* and other Apicomplexan Parasites by Hybridization and PCR", *Molecular and Cellular Probes,* vol. 10, pp. 289–297, 1996.

Lappin, M., et al., "Polymerase Chain Reaction for the Detection of *Toxoplasma gondii* in Aqueous Humor of Cats", *American J. Vet. Res.,* vol. 57(11), pp. 1589–1593, Nov., 1996.

Stiles, J., et al., "Detection of *Toxoplasma gondii* in Feline and Canine Biological Samples by Use of the Polymerase Chain Reaction", *American J. Vet. Res.,* vol. 57(3), pp. 264–267, Mar., 1996.

Owen, M., et al., "Diagnosis of Toxoplasma Abortion in Ewes by Polymerase Chain Reaction", *The Veterinary Record,* vol. 142, pp. 445–448, Apr. 1998.

Luo, W., et al., "Kinetics in Parasite Abundance in Susceptible and Resistant Mice Infected with an Avirulent Strain of *Toxoplasma gondii* by Using Quantitative PCR", *J. Parasitology,* vol. 83(6), pp. 1070–1074, 1997.

Jenum, P., et al., "Diagnosis of Congenital *Toxoplasma gondii* Infection by Polymerase Chain Reaction (PCR) on Amniotic Fluid Samples", *APMIS,* vol. 106, pp. 680–686, 1998.

Esteban–Redondo, I., et al., "Dectection of *T. gondii* in Tissues of Sheep and Cattle Following Oral Infection", *Veterinary Parasitology,* vol. 86, pp. 155–171, 1999.

* cited by examiner

SEQUENCE LISTING

<160> NUMBER OF SEQ ID NOS: 8

<210> SEQ ID NO 1
<211> LENGTH: 28
<212> TYPE: DNA
<213> ORGANISM: Toxoplasma gondii

<400> SEQUENCE: 1
gatttgcatt caagaagcgt gatagtat                                      28

<210> SEQ ID NO 2
<211> LENGTH: 28
<212> TYPE: DNA
<213> ORGANISM: Toxoplasma gondii

<400> SEQUENCE: 2
agtttaggaa gcaatctgaa agcacatc                                      28

<210> SEQ ID NO 3
<211> LENGTH: 21
<212> TYPE: DNA
<213> ORGANISM: Toxoplasma gondii

<400> SEQUENCE: 3
ctgcgctgct tccaatattg g                                             21

<210> SEQ ID NO 4
<211> LENGTH: 18

-continued

```
<212> TYPE: DNA
<213> ORGANISM: Unknown
<220> FEATURE:
<223> OTHER INFORMATION: Universal Sequence of Unknown Origin

<400> SEQUENCE: 4
cggctaccac atctaagg                                                18

<210> SEQ ID NO 5
<211> LENGTH: 19
<212> TYPE: DNA
<213> ORGANISM: Unknown
<220> FEATURE:
<223> OTHER INFORMATION: Universal Sequence of Unknown Origin

<400> SEQUENCE: 5
tatacgctat tggagctgg                                               19

<210> SEQ ID NO 6
<211> LENGTH: 25
<212> TYPE: DNA
<213> ORGANISM: Mouse

<400> SEQUENCE: 6
tcacccacac tgtgcccatc tacga                                        25

<210> SEQ ID NO 7
<211> LENGTH: 25
<212> TYPE: DNA
<213> ORGANISM: Mouse

<400> SEQUENCE: 7
cagcggaacc gctcattgcc aatgg                                        25

<210> SEQ ID NO 8
<211> LENGTH: 24
<212> TYPE: DNA
<213> ORGANISM: Mouse

<400> SEQUENCE: 8 atgcccccccc atgccatcct gcgt                                         24
```

POLYMERASE CHAIN REACTION ASSAY FOR THE DETECTION OF *TOXOPLASMA GONDII*

BACKGROUND OF THE INVENTION

Field of the Invention

*Toxoplasma gondii* (*T. gondii*) is an intracellular protozoan parasite which infects a wide variety of animals. This invention relates to novel primers which can be utilized in a polymerase chain reaction (PCR) assay to detect and quantitate the presence of *T. gondii* in test samples.

Description of the Related Art

*T. gondii* can exist in all mammals and is believed to persist for the life of its host as cysts in muscle tissue or in the central nervous system. The cysts may rupture, releasing tachyzoites, which are the highly infective stage of the parasite and responsible for the onset of toxoplasmosis, a disease which is potentially fatal in individuals having compromised immune systems. Tachyzoites differentiate into bradyzoites which are located within the cysts and may convert back into the infectious tachyzoite stage should the immune system of the host fail or become compromised.

Toxoplasmosis is one of the most prevalent parasitic diseases in human beings and agricultural animals. Mead et al. (1999. *Emerg. Infect. Dis.* vol. 5, pp. 605–625) have estimated that approximately 225,000 new cases are reported each year in the U.S., and 50% of the cases are believed to be due to the food borne transmission of *T. gondii*. The National Hospital Discharge survey indicated that toxoplasmosis was the first diagnosis for approximately 5,000 discharges each year during 1992 to 1996, including 750 deceased patients. Furthermore, 4,000 persons with AIDS will develop toxoplasmic encephalitis in the U.S. each year (Mead et al., supra). In addition, toxoplasmosis may occur during pregnancy in mothers who have not previously been infected with the parasite. From an economic point of view, *T. gondii* infection has a negative impact on society as measured by increases in the costs of chemotherapy in AIDS patients (Freedberg et al. 1998. *J. Am. Med. Assoc.* vol. 279, pp. 130–136), serological screening in pregnant women, patient care, loss of productivity and the treatment of infected mothers and children (Lappalainen et al. 1995. *Scan. J. Infect. Dis.* vol. 27, pp. 265–272).

*T. gondii* can be transmitted to humans by ingesting *T. gondii* oocysts in food or water or by consuming tissue cysts in raw or undercooked meat. Infected pork is considered the most important meat source of *T. gondii* in the U.S. (Dubey, J. P. 1994. *J. Am. Vet. Med. Assoc.* vol. 205. pp. 1593–15984). Considering the potentially serious consequences of congenital *T. gondii* infection in humans, such as birth defects, retinitis, brain damage, or even death, it is essential that efforts be directed at preventing food borne transmission.

The detection of *T. gondii* cysts in tissues of naturally and experimentally infected pigs and sheep has been reported for years (Dubey et al. 1986. *J. Am. Vet. Med. Assoc.* vol. 188, pp. 1035–1037; Jacobs et al. 1960. *J. Parasitol.* vol. 46, pp. 23–28), although the prevalence of *T. gondii* infection in U.S. pig populations has been dramatically reduced as producers have modified their management practices (Weigel et al. 1995. *J. Parasitol.* vol. 81, pp. 736–741). A true *T. gondii* burden in any food product has been difficult to measure, however, and to date, the most reliable method of food inspection for *T. gondii* has been to demonstrate the presence of *T. gondii* tissue cysts by in vivo biological assays (Esteban-Redondo et al. 1999. *Vet. Parasitol.* vol. 86, pp. 155–171; Gamble and Murrell. 1998. *Parasitology.* vol. 117, pp. S97–111). Because these methods are costly, time-consuming and often unreliable, they are not suitable for slaughterhouse testing or for monitoring commercial meat products (Gamble and Murrell, supra).

There have been many reports of molecular-based assays for the diagnosis of toxoplasmosis, but most have been developed for human diagnostics (Costa et al. 2000. *J. Clin. Microbiol.* vol. 38, pp. 2929–2932; Dupon et al. 1995. *J. Clin. Microbiol.* vol. 33, pp. 2421–2426; Jenum et al. 1998. *Acta Pathol. Microbiol. Immunol. Scand.* vol. 106, pp. 680–686) or phylogenetic studies (Carreno and Barta. 1999. *J. Parasitol.* vol. 85, pp. 77–83; Ellis et al. 1998. *Mol. Cell. Probes.* vol. 12, pp. 1–13; Kaufman et al. 1996. *Mol. Cell. Probes.* vol. 10, pp. 289–297). In veterinary medicine, tests for detection of *T. gondii* by PCR were reported mostly for companion animals (Lappin et al. 1996. *Am. J. Vet. Res.* vol. 57, pp. 1589–1593; Stiles et al. 1996. *Am. J. Vet. Res.* vol. 57, pp. 264–267) or sheep (Esteban-Redondo and Innes. 1998. *Int. J. Parasitol.* vol. 28, pp. 1459–1466; Owen et al. 1998. *Vet. Rec.* vol. 142, pp. 445–448), though Warnekula-suriya et al. (1998. *Int. J. Food Microbiol.* vol. 45, pp. 211–215) reported using PCR to identify *T. gondii* in cured meat products. Several studies have been directed at quantitating the actual *T. gondii* burden in biological fluids or tissues, but these involved time-consuming PCR protocols (competitive PCR) followed by agarose gel image analysis (Homan et al. 2000. *Int. J. Parasitol.* vol. 30, pp. 69–75; Kirisits et al. 2000. *Int. J. Parasitol.* vol. 30, pp. 149–155; Luo et al. 1997. *J. Parasitol.* vol. 83, pp. 1070–1074). Costa et al. (supra) addressed the quantitation issue with a real-time PCR analysis of *T. gondii* in human serum samples from stem cell-transplanted patients; however, this assay was based on the *T. gondii* B1 gene and not the more abundant rRNA gene.

SUMMARY OF THE INVENTION

We have designed novel oligonucleotide sequences which are capable of uniquely amplifying DNA from *T. gondii* when utilized in a PCR assay. In addition, a probe has also been designed which is effective in PCR assays for the detection of *T. gondii* amplification products. The novel probe is particularly effective when utilized as a fluorogenic probe in a real time PCR assay.

Accordingly, it is an object of the invention to provide novel oligonucleotides for use as primers in a PCR assay for the detection and/or quantitation of *T. gondii*.

It is another object of the invention to provide a novel probe for use with the novel primers for the detection and/or quantitation of *T. gondii*, preferably a fluorogenic probe for use in a fluorogenic real time PCR assay.

It is a further object of the invention to provide PCR assay methods for the detection of *T. gondii* utilizing the novel primers.

Other objects and advantages of the invention will become readily apparent from the following description.

BRIEF DESCRIPTION OF THE DRAWINGS

FIG. 2 shows the results of sensitivity studies for the fluorogenic real time assay. In panel A, results are shown for dilutions of T. gondii DNA [100 ng (A), 10 ng (B), 1 ng (C), 100 pg (D), 10 pg (E), 1 pg (F) 0.1 pg (G) and 0.01 pg (H)] and no template controls (NTC) assayed. In panel B, electrophoresed and ethidium bromide-stained PCR products are shown. In panel C, a plot of mean $C_T$ values from 8 replicates, tested on different days, against the T. gondii DNA inputs (log pg) is shown. Variability is shown as the mean $C_T$ values±1 SD. The plot of the $C_T$ values and DNA input fits a linear function ($R^2$=0.9985).

FIG. 3 shows the precision of the fluorogenic real time PCR assay. Intra-assay precision is represented by the mean $C_T$ value from 10 replicates tested simultaneously (white bars) for samples of genomic T. gondii DNA at 1 ng, 100 pg and 10 pg and a bradyzoite-spiked pig sample (sample A). Repeatability is represented by the mean $C_T$ values±1 SD from 4 replicates of the same T. gondii DNA samples analyzed on 5 different days (black bars).

DETAILED DESCRIPTION OF THE INVENTION

The PCR assay is known to be highly sensitive and specific for the detection and/or quantitation of microorganisms. A number of PCR assays have been developed for the detection of T. gondii targeting mainly the B1 repetitive sequence, the P30 surface antigen gene, ribosomal DNA (rDNA) or small subunit ribosomal RNA (SSUrRNA) as described in Guay et al. 1993. J. Clin. Microbiol. vol. 31 (2), pp. 203–207; Johnson et al. 1990. Abstract, Transactions-Biochemical Society, vol. 18, p. 665; Costa et al., supra; Tenter et al. 1994. Appl. Parasitol. vol. 35, pp. 173–188; Warnekulasuriya et al., supra; Ellis, J. T. 1998. Intl. J. Parasitol. vol. 28, pp. 1053–1060. Enzymatic amplification of targeted sequences is carried out according to conventional procedures (as described, for example, in Mullis, U.S. Pat. No. 4,683,202, herein incorporated by reference). Briefly, a target DNA sequence serves as a template and is amplified utilizing at least one primer or primer pair and a thermostable DNA polymerase. The primers hybridize to either the target sequence or to a sequence flanking the target sequence, and the polymerase extends the primer(s) using the target sequence as a template, resulting in the synthesis of extension products which are complementary to each nucleic acid strand of the target DNA sequence. Extension products synthesized from each primer serve as a template for the other primer. An amplification cycle consists of heat denaturing the target DNA of a test sample, annealing the primers to their complementary sequences and extending the primers with thermostable DNA polymerase (e.g. Taq polymerase). The amplification cycle is repeated in order to increase the number of amplified target DNA sequences sufficient to produce a detectable quantity of DNA which is indicative of the presence of the analyte in question. Primers are oligonucleotides which hybridize to DNA strands having the coding sequence of a target sequence (sense primers) or hybridize to DNA strands that are complementary to the coding sequence of a target sequence (anti-sense primers).

Following amplification, the DNA product may be separated from the reaction mixture and analyzed by, for example, electrophoresis in agarose or polyacrylamide gel (PAGE) and detected by any means effective for detecting DNA. Such detection means are well-known to those of skill in the art. A detectable label, such as a radioactive, calorimetric, fluorometric or luminescent signal or organic substituent such as biotin, or chemical staining, such as with ethidium bromide, silver stain or other DNA dyes, may be utilized. Analysis of the amplified products may also be carried out by Southern blot or dot blot hybridization assays.

In the present invention, the following primers are effective for the specific amplification of target DNA from T. gondii:

5'-GATTTGCATTCAAGAAGCGTGATAGTAT-3' (sense) (SEQ ID NO: 1) and

5'-AGTTTAGGAAGCAATCTGAAAGCACATC-3' (anti-sense) (SEQ ID NO: 2).

The primers may be labelled, as previously mentioned, or a labelled probe may be utilized for detection of amplification product. An effective probe is:

5'-CTGCGCTGCTTCCAATATTGG-3' (SEQ ID NO: 3).

Useful labels include, but are not limited to, radioactive, calorimetric, fluorescent or luminescent and organic. For example, when utilizing the probe of SEQ ID NO: 3, a fluorescent reporter molecule at the 5' end and a fluorescence quencher molecule at the 3' end of the probe has been shown to increase sensitivity when used in the real time assay systems:

5'-6-FAM-CTGCGCTGCTTCCAATATTGG-TAMRA-3' (SEQ ID NO: 3), where FAM is the fluorescent reporter molecule 6-carboxifluorescein and TAMRA is the fluorescence quencher molecule 6-carboxitetramethyl-rhodamine. These primers and probe were derived from the internal transcribed spacer 1 (ITS1) region of the T. gondii 18S rRNA gene (Table 1). Real time assay systems record results over the entire course of the PCR reaction time. Sequence analysis is described in Example 1.

For the detection of T. gondii, the novel primers may be utilized in a conventional PCR assay method (as, for example, described by Mullis, supra). Briefly, such a method is carried out by providing a test sample suspected of containing T. gondii DNA, amplifying said DNA with primers SEQ ID NO: 1 and SEQ ID NO: 2 and detecting the presence of amplified DNA as an indication of

TABLE 1

Sequences of Primers and Probes Utilized in PCR Detection of T. Gondii.

| Gene | Primer/Probe Sequences |
| --- | --- |
| T. gondii ITS1 | 5'-GATTTGCATTCAAGAAGCGTGATAGTAT-3' (sense) (SEQ ID NO: 1) |
| | 5'-AGTTTAGGAAGCAATCTGAAAGCACATC-3' (anti-sense) (SEQ ID NO: 2) |
| | 5'-CTGCGCTGCTTCCAATATTGG-3' (probe) (SEQ ID NO: 3) |
| Universal 18SrRNA | 5'-CGGCTACCACATCTAAGG-3' (sense) (SEQ ID NO: 4) |
| | 5'-TATACGCTATTGGAGCTGG-3' (anti-sense) (SEQ ID NO: 5) |
| Mouse (Hu) β-Actin | 5'-TCACCCACACTGTGCCCATCTACGA-3' (sense) (SEQ ID NO: 6) |
| | 5'-CAGCGGAACCGCTCATTGCCAATGG-3' (sense) (SEQ ID NO: 7) |
| | 5'-6-FAM-ATGCCC-x(TAMRA)-CCCCATGCCATCCTGCGT-3' (probe) (SEQ ID NO: 8) | the presence of T. gondii. The test sample may be a biological sample comprising T. gondii parasites or extracted DNA. Detection may be carried out utilizing the probe SEQ ID NO: 3.

Methods have thus been developed for direct PCR utilizing the primers of SEQ ID NOS: 1 and 2. In a further development, fluorogenic PCR methods which utilize an instrument such as the ABI PRISM® 7700 Sequence Detection System (Applied Biosystems, Foster City, Calif.) and the probe of SEQ ID NO: 3 for the real time detection of PCR amplification products has been found particularly effective for increasing the sensitivity and specificity of the assay (see Example 2) and for quantitation of the amount of T. gondii present in a given sample. This fluorogenic real time PCR assay system is therefore used for purposes of discussion herein.

The fluorogenic real time assay is a PCR-based assay which requires an oligonucleotide probe containing a fluorescent reporter/fluorescence quencher pair. The probe is designed so that the quencher molecule is located sufficiently close to the reporter molecule to ensure that the fluorescence of the reporter molecule is normally quenched. The probe binds to a site located between that of the primers used to amplify the target DNA. During strand extension by DNA polymerase, preferably TAQ DNA polymerase AMPLITAQ® (Perkin-Elmer, Norwalk, Conn.), annealed probe containing the reporter/quencher pair is digested by exonuclease activity of Taq polymerase. This digestion results in separation of the reporter molecule from the quencher molecule so that the quencher molecule is no longer in close enough proximity to the reporter molecule to quench its fluorescence. Thus, as more PCR product is synthesized, a concomitant proportion of more annealed probes are digested during amplification. This results in an increase in unquenched reporter molecules in the reaction mixture, ultimately resulting in an increase in the fluorescent signal produced during consecutive cycles.

Figure 1A:
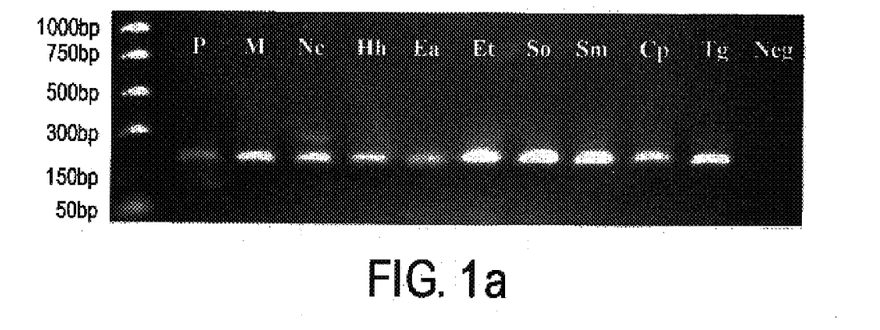
FIG. 1 shows a comparison of the amplification of parasite and host DNA samples using direct PCR and fluorogenic real time assay methods. Analyses were performed by direct PCR using universal 18S rRNA primers (panel A) or *T. gondii* ITS1 primers (panel B) or by real time PCR (panel C).
Figure 1B:
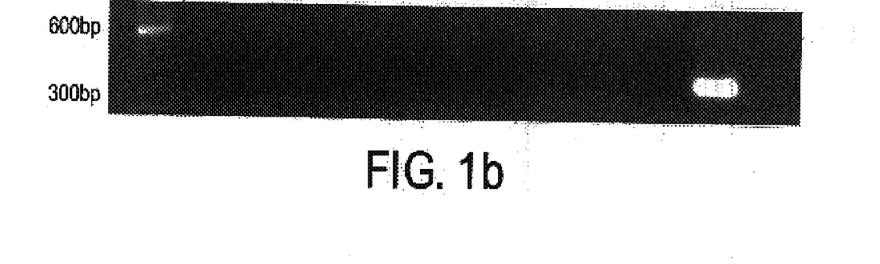
Figure 1C:
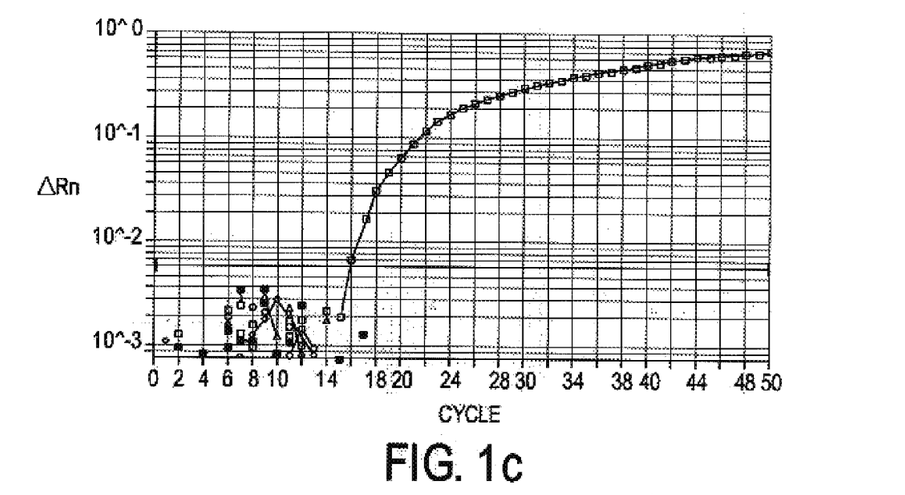

Comparison studies (see example 3) were carried out to confirm assay specificity utilizing DNA samples from T. gondii (see Example 4) and other common protozoa (Neospora caninum, Hammondia hammondi, Eimeria acervulina, Eimeria tenella, Cryptosporidium parvum, Sarcocystis muris, Sarcocystis ovicanis) as well as host animal tissue (see Example 5). Results are shown in FIG. 1. Analyses were performed by direct PCR using universal 18S rRNA primers (SEQ ID NOS: 4 and 5, Table 1), FIG. 1A, and T. gondii ITS1 primers, FIG. 1B, or by fluorogenic real time PCR assay, FIG. 1C. Direct PCR is considered any PCR assay method which does not utilize a probe as a detection means. The universal primers are complementary to rDNA for all species and confirm the presence of DNA in a sample, i.e. a positive control.

The fluorogenic real time PCR assay was performed as described in Example 2. DNA from all parasite and host samples included in the test panel were amplified by the universal 18S rDNA primers, generating bands of similar intensity (FIG. 1A), thus confirming the quality of DNA in the test sample and that equal amounts of DNA were loaded per reaction. The T. gondii primers only reacted with T. gondii DNA, generating a DNA fragment of ~333 bp, as expected based on its known sequence (FIG. 1B). No PCR products were observed with any other DNA samples tested. All samples were also analyzed using the fluorogenic real time PCR assay, and only the T. gondii DNA gave a strong positive response, with a $C_T$ value of ~16 (FIG. 1C).

The $C_T$ value is defined as the cycle number at which the reporter fluorescence exceeds the threshold value, a parameter defined by 10 standard deviations (SD) above the baseline fluorescence. The $C_T$ value may be serve as an indication of T. gondii DNA quantity; and the lower the $C_T$ value, the higher the amount of T. gondii DNA present in the test sample and vice versa.

Figure 2A:
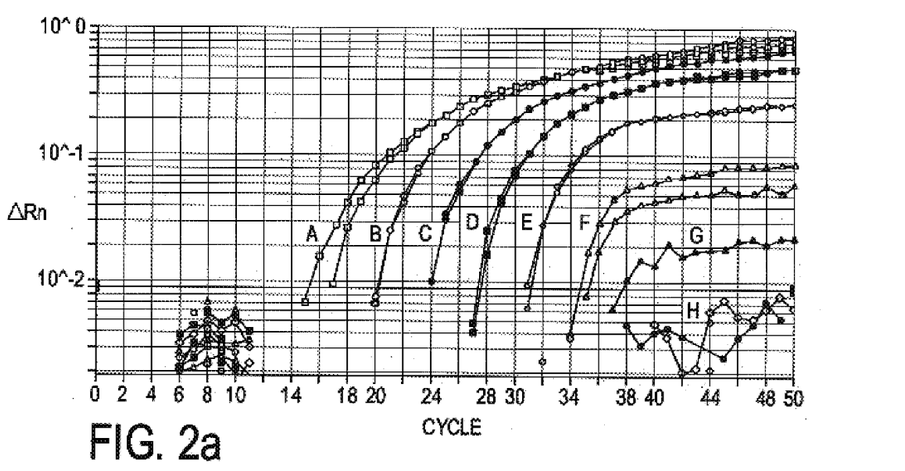

Experiments were also carried out to evaluate the sensitivity of the fluorogenic real time PCR assay. Amplifications of 10-fold dilutions of a T. gondii genomic DNA were performed, and dilution series of from 100 ng to 10 fg of T. gondii DNA were tested in duplicate (see Example 6). Results are shown in FIG. 2 where FIG. 2A shows a typical real-time display of a fluorogenic real time PCR assay provided by the ABI Prism® 7700 instrument (Applied Biosystems, supra). Positive signals ($C_T$ values) were found for all dilutions except the sample containing 10 fg T. gondii DNA. Thus, a detection limit of 0.1 pg T. gondii DNA, or DNA equivalent to 1 bradyzoite, was achieved.

Figure 2B:
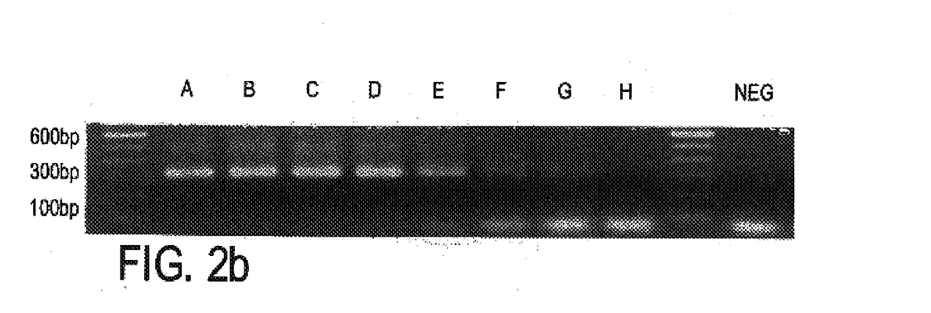

The PCR products generated by the fluorogenic real time assay process were electrophoresed in agarose gel and stained with ethidium bromide. In agreement with the $C_T$ values, bands of the expected size (~333 bp) were detected down to 100 fg T. gondii DNA, although the bands for 1 pg and 0.1 pg were dim (FIG. 2B).

Figure 2C:
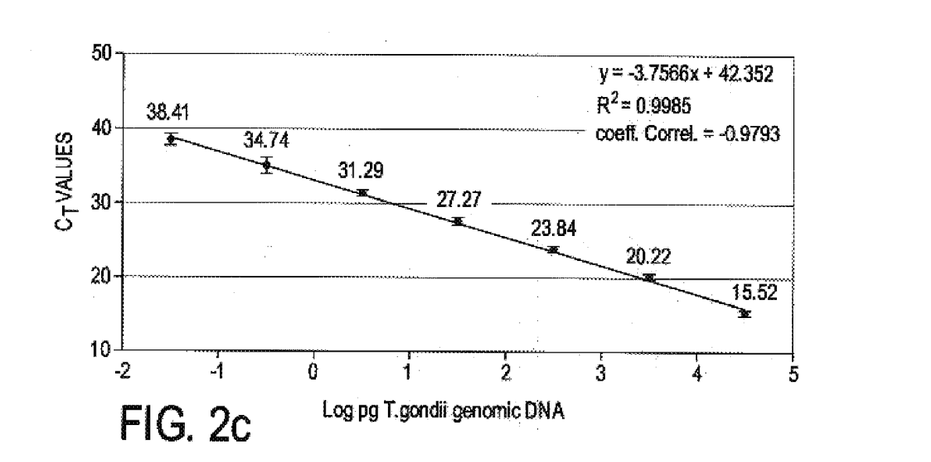

Mean $C_T$ values from 8 replicates of the series of T. gondii concentrations were calculated (FIG. 2C). These values ranged from 15.52±0.21 for 100 ng of *T. gondii* genomic DNA to 38.4±0.64 for 0.1 pg and showed reproducible linearity over seven orders of magnitude ($R^2=0.9984$). A significant coefficient of correlation was found for the mean $C_T$ values and *T. gondii* DNA concentrations (r=−0.9793).

Figure 3:
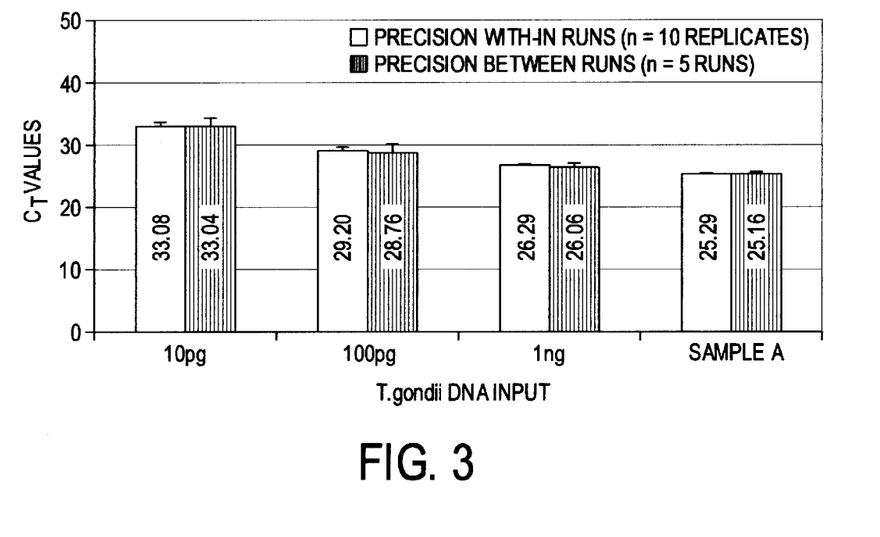

Fluorogenic real time PCR assay precision was also tested for both intra- and inter-assay. Results are shown in FIG. 3. Intra-assay precision (FIG. 3, white bars) was measured on 10 replicates of *T. gondii* DNA concentrations of 1 ng, 100 pg and 10 pg and samples of muscle from a *T. gondii*-free pig spiked at ~3.7×10⁴ bradyzoites/1 g muscle tissue. The samples were tested simultaneously and expressed. as mean $C_T$ values. Results showed low variability with a CV of <1.75% for the lowest *T. gondii* genomic DNA concentration (10 pg) and <1% for the *T. gondii*-spiked sample. Inter-assay precision (FIG. 3, black bars) was measured on 20 replicates, 4 replicates of the same *T. gondii* DNA samples analyzed on 5 different days, and expressed as mean $C_T$ values. Results showed a CV of 4.5% for *T. gondii* genomic DNA and of 1.7% for the *T. gondii*-spiked pig muscle sample.

identified correctly (Table 2). Good correlation between $C_T$ values and titers obtained from a modified agglutination test (Desmont and Remington. 1980. *J. Clin. Microbiol.* vol. 11, pp. 562–568) was observed for the pig DNA samples (r=−0.719). All fluorogenic real time $C_T$ values from mouse DNA samples were normalized against $C_T$ values generated with the β-actin TaqMan® (Applied Biosystems, supra) kit (see Table 1 for β-actin primer and probe sequences), a standard for the real time assay which serves as a positive control within the assay format (Table 2). These data confirmed that the fluorogenic real time PCR assay was positive when tested against DNA from each of the three known *T. gondii* genotypes (Example 4).

It has thus been demonstrated that the fluorogenic real time PCR assay is a very sensitive specific assay that can be used to successfully detect the presence of *T. gondii* in

TABLE 2

Fluorogenic Real Time PCR Assay Results Testing Samples from *T. Gondii*-Infected Pigs and Mice[a]

| Animal ID | *T. Gondii* Strain | Inoculum | Antibodies to *T. Gondii*[b] | *T. gondii* $C_T$ Values | β-Actin $C_T$ Values | Normalized *T. gondii* $C_T$ values[c] |
|---|---|---|---|---|---|---|
| M 7076 | VEG | 200 B[d] | ≥1:50 | 24.69 | 25.86 | 21.96 |
| M 7077 | VEG | 200 B | ≥1:50 | 24.51 | 27.84 | 23.46 |
| M 7078 | VEG | 200 B | ≥1:50 | 25.49 | 28.16 | 24.68 |
| M 7079 | VEG | 200 B | ≥1:50 | 27.2 | 27.64 | 25.85 |
| M 7080 | VEG | 200 B | ≥1:50 | 25.05 | 27.82 | 23.96 |
| M 8348 | Me49 | 1 T[e] | ≥1:200 | 28.84 | 28.84 | 28.44 |
| M 8349 | Me49 | 1 T | ≥1:200 | 29.41 | 28.23 | 29.19 |
| M 8350 | Me49 | 1 T | ≥1:200 | 29.39 | 27.25 | 28.16 |
| M 8351 | Me49 | 1 T | ≥1:200 | 29.19 | 27.31 | 28.03 |
| MP 521 | VEG | 500 O[f] | 1:800 | 32.26 | N/D | N/D |
| MP 522 | VEG | 500 O | 1:1,1600 | 30.33 | N/D | N/D |
| MP 523 | VEG | 500 O | 1:400 | 32.24 | N/D | N/D |
| MP 524 | VEG | 500 O | 1:200 | 33.52 | N/D | N/D |
| MP 526 | VEG | 500 O | 1:800 | 32.09 | N/D | N/D |
| MP 490 | None | 0 | <1:25 | ≥50 | N/D | N/D |
| MP 532 | None | 0 | <1:25 | ≥50 | N/D | N/D |

[a]DNA samples from Swiss Webster mice (M), 500 ng total input, and NIH minipigs (MP), 1 μg, infected with different *T. gondii* strains were analyzed by fluorogenic real time PCR assay. DNA was obtained from brain tissues as described in Example 4. Tachyzoites and bradyzoites were injected subcutaneously and oocysts orally inoculated.
[b]Specific antibody detection was performed by MAT as described in Example 7.
[c]Normalization factor: Toxo $C_T$ value x (β-actin $C_T$ sample/highest β-actin $C_T$ value).
[d]Counted bradyzoites (B).
[e]Number of tachyzoites (T) determined by bioassay in mice. This dilution (10⁻⁵) was infective to all 4 mice; 10⁻⁶ dilution was not infective to any 4 mice.
[f]Approximate number of live oocysts (O) determined by dilution bioassay in mice.

Figure 4A:
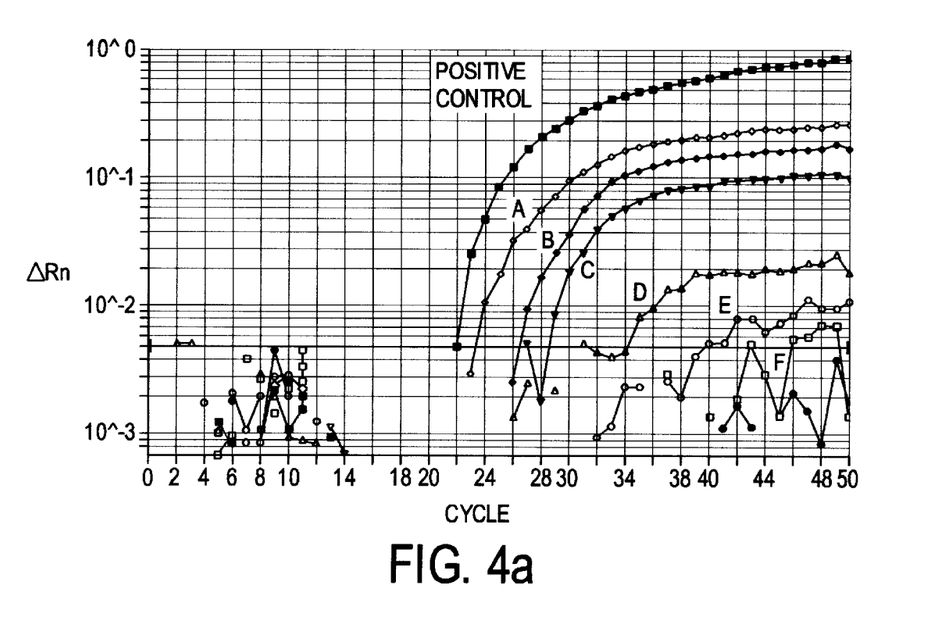
FIG. 4 shows the detection of T. gondii DNA in bradyzoite-spiked pig muscle samples. Panel A shows six 1-g muscle samples obtained from a T. gondii-free pig spiked with known numbers of T. gondii bradyzoites (A, $3.7 \times 10^5$; B, $3.7 \times 10^4$; C, $3.7 \times 10^3$; D, $3.7 \times 10^2$; E, $3.7 \times 10^1$; F, $<4 \times 10^0$). Panel B shows the mean $C_T$ values±1 SD from 8 replicates run on 4 different days plotted against the log number of T. gondii bradyzoites. Linearity is observed over the whole range of bradyzoite numbers ($R^2$=0.9776).
Figure 4B:
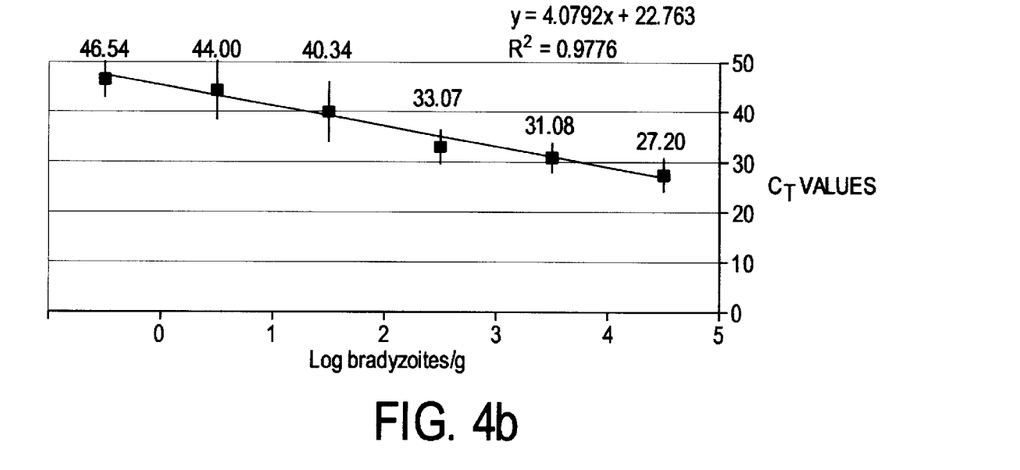

The capability of the fluorogenic real time PCR assay for detecting *T. gondii* in animal tissue was also evaluated. Six 1-g muscle tissue samples were obtained from a *T. gondii*-free pig. The samples were spiked with 3.7×10⁵, 3.7×10⁴, 3.7×10³, 3.7×10², 3.7×10¹ and <4×10⁰ bradyzoites/sample. Results are shown in FIG. 4. All samples gave positive signals with mean $C_T$ values ranging from 27.2 to 46.5 (FIG. 4A). The fluorogenic real time PCR assay was linear for over six logs of bradyzoite concentrations ($R^2=0.9776$, FIG. 4B). A significant coefficient of correlation (r=−0.68) between number of bradyzoites and $C_T$ values was observed.

In addition to testing *T. gondii*-spiked animal tissue, samples from animals experimentally infected with *T. gondii* were also analyzed (as described in Example 7). The fluorogenic real time PCR assay of samples from experimentally infected pigs and mice corresponded well with their serological status; i.e. all infected and control animals were biological samples using the novel *T. gondii*-specific ITS1 primers alone or in combination with a fluorogenic probe. The detection response was linear over a range of 7 logs of *T. gondii* DNA concentrations ($R^2=0.9985$), as well as parasite numbers ($R^2=0.9776$), and as little as 0.1 pg of *T. gondii* genomic DNA was detectable. The fluorogenic real time PCR assay presents several important advantages over other methods of detection and quantitation of *T. gondii* DNA. First, fluorogenic real time PCR is performed in a closed tube with no post-PCR manipulations, thereby reducing potential PCR product carry-overs and post-PCR processing time. Second, the assay is quick and results can be confirmed within one day. Third, the assay response is sensitive and linear over a broad range of DNA concentrations. Finally, sample processing is compatible with current PCR-based automation technology (Heid et al. 1996. *Genome Res.* vol. 6, pp. 986–994).

The sensitivity limit with the fluorogenic real time PCR assay is similar to that reported elsewhere for *T. gondii* despite differences in the target gene (Costa et al., supra; Jenum et al., supra; Lappin et al., supra) and exhibits a linear range of detection ($R^2$=0.9985) similar to Costa et al. (supra). Furthermore, the fluorogenic real time PCR assay shows a two-fold better sensitivity than other PCR tests (James et al. 1996. *J. Clin. Microbiol.* vol. 34, pp. 1572–1575; Owen et al., supra; Stiles et al., supra), which detected ~10 parasites in diverse biological samples. In these studies, *T. gondii* DNA extractions were performed from a variety of samples, such as serum (Costa et al., supra), aqueous humor (Lappin et al., supra), amniotic fluid (Homan et al., supra) or cell culture (James et al., supra), where contaminating host-derived DNA was low and therefore cannot be equated to the fluorogenic real time PCR assay which was performed on as much as 50 g of pig tissue.

When applying the assay on bradyzoite-spiked muscle samples, the fluorogenic real time PCR test successfully detected as few as ~4 bradyzoites per gram of pig tissue. This sensitivity level is substantially better than that reported by Warnekulasurizy et al. (supra) on cured meats ($5 \times 10^3$ tachyzoites/g), who attributed this low sensitivity to the high salt content of the cured meat. Considering that the fluorogenic real time results were linear ($R^2$=0.9776) and detected from as few as 4 parasites to as many as $3.7 \times 10^5$ parasites per gram of tissue, the range of detection is not a limitation. Other investigators have reported a range of detection of only $10^2$–$10^4$ *T. gondii* organisms using a quantitative competitive PCR with the B1 gene (Kirisits et al., supra) or with a highly repetitive DNA sequence as the target gene (Homan et al., supra). Costa et al. (supra) detected from 1 to ~400 parasites in 200 µl serum samples of stem cell transplanted patients using a LightCycler based PCR test.

It is difficult to find *T. gondii* cysts in tissues from large animal species due to several factors, including sampling bias and parasite predilection sites. Dubey et al. (1996. *J. Parasitol.* vol. 82, pp. 438–443) have estimated that less than 1 tissue cyst/50 g of tissue is likely to be found in *T. gondii*-infected pigs. Thus, it is possible that, when performing any test for tissue cyst detection, false negatives can result from insufficient sample size or improper sample acquisition (Esteban-Redondo et al., supra). In the studies described supra, it was assumed that the pigs inoculated with *T. gondii* might harbor low numbers of cysts in their tissues, despite a moderate infective dose (500 oocysts). Therefore, digestion/concentration steps were applied for some samples, e.g. the 50-g brain or tonguein order to reduce the actual amount of host tissue undergoing DNA extraction. Since $C_T$ values in the fluorogenic real time PCR assay correspond with the number of bradyzoites per gram (r=−0.68), a standard curve using samples spiked with known numbers of *T. gondii* tachyzoites or bradyzoites can be constructed, allowing the extrapolation of the *T. gondii* burden in unknown samples from the $C_T$ values, i.e. quantitation of the amount of *T. gondii* in a specific sample. In addition, analyses may be carried out using multiplex real time PCR assays utilizing different fluorogenic probes.

The capability of the fluorogenic real time PCR assay to correctly identify *T. gondii*-infected animals with a high degree of sensitivity was demonstrated for both parasite-infected mice and pigs and was shown to work on multiple states of infection, i.e. both bradyzoite and tachyzoite (Table 2). The results were corroborated both by the serological responses of all infected animals and by the presence of tissue cysts in the brains of infected mice. Furthermore, a significant association between antibody titers of pigs and $C_T$ values was observed (r=−0.719). As in other quantitative methods (Costa et al., supra; Homan et al., supra; Kirisits et al., supra), the fluorogenic real time PCR assay is dependent on the initial DNA input; thus standardization by a normalization gene such as the β-actin gene is recommended. It is noted that such normalization genes are known in the art (and may be referred to as "housekeeping" genes) and are commercially available. The use of the β-actin gene specifically is not required.

Serological testing has previously been the only practical tool for the identification of *T. gondii* infection in pigs, either in food animal inspections or epidemiological studies (Gamble et al. 1999. *Vet. Parasitol.* vol 82, pp. 129–136). With the development of the fluorogenic real time PCR assay, however, current indirect serology testing can be supplemented or replaced with the more direct assay. The contamination of commercial meat products by *T. gondii* can be monitored more effectively with the expectation of ultimately reducing the foodborne transmission of this harmful parasite. For example, random sampling can be carried out in slaughterhouses, packing houses, processed food preparation factories or grocery stores. Samples include, but are not limited to, pork and lamb products. As consumption of more exotic meats, such as ostrich, emu, horsemeat, etc., increases, screening for food borne zoonotics such as *T. gondii* becomes more important. Moreover, the assay will also provide an objective tool for quantitating *T. gondii* burden for vaccination studies and clinical trials for therapeutic treatments or for improving management based on Hazard Analysis for Critical Control Points (HACCP) principles.

The following examples are intended only to further illustrate the invention and are not intended to limit the scope of the invention as defined by the claims.

All references cited herein are herein incorporated by reference.

EXAMPLES

Example 1

Sequence Analysis

In order to identify the sequences of the primers, alignment of the ITS1 region of the 18S rRNA gene sequences from *T. gondii* (Genbank access # X75429.1, RH strain) and other coccidian parasites such as *N. caninum* (Genbank access # AF038861, NC-1 isolate), *H. hammondi* (Genbank access # AF096499.1), and *Hammondia heydorni* (Genbank access # AF076858.1) was performed using the UWGCG sequence analysis software package (GCG Version 10.0, Genetics Computer Group, Madison, Wis.). This region was selected because it has been reported to have a high rate of nucleotide substitutions (Carreno and Barta, supra). Primer and probe sequences for detection of *T. gondii* and for normalization with housekeeping genes are shown in Table 1.

Example 2

Fluorogenic Real Time PCR Assay for Detection of *T. gondii*.

The real time assay for *T. gondii* uses a specially designed fluorogenic probe and primers (Table 1), and directly relates the amount of initial target gene with the reporter's fluorescence emission (Heid et al., supra). The fluorogenic probe sequence was designed using the software Primer Express (version 1, Applied Biosystems, supra) and synthesized with the reporter dye (FAM, 6-carboxifluorescein) at the 5' end and the quencher molecule (TAMRA, 6-carboxitetramethyl-rhodamine) covalently coupled to the 3' end (Table 1).

For the fluorogenic real time PCR assay, a 50 µl mixture containing 1×TaqMan® buffer A [10 mM Tris HCl, pH 8.3, 500 mM KCl, 0.1 M EDTA, 600 mM ROX, Applied Biosystems, supra], 1.5 mM MgCl$_2$, 1 µM of each T. gondii ITS1 primer, 200 nM fluorogenic probe, 200 µM of each deoxynucleotide triphosphate, 1 U of AmpliTaq Gold® DNA polymerase (Applied Biosystems, supra) was prepared and up to 1 µg of the template DNA was tested. After activation of the AmpliTaq Gold® DNA polymerase for 10 min at 95° C., PCR was performed for 50 cycles of 15 sec at 94° C. followed by 1 min at 60° C. The products were analyzed on an ABI PRISM® 7700 Sequence Detection (Applied Biosystems, supra). All the data acquisition and data analyses were performed with Sequence Detector Software (SDS version 1.7, Applied Biosystems, supra), and $C_T$ values were recorded for statistical analysis on Excel spreadsheets.

Detection of the mouse β-actin housekeeping gene was performed with a commercially available TaqMan® kit developed for human β-actin (Applied Biosystems, supra), using 35 cycles (see Table 1 for primer and probe sequences). Conditions for mouse β-actin were similar to those described for the fluorogenic real time PCR assay, except annealing temperature was decreased to 52° C. MgCl$_2$ concentration was decreased to 1.5 mM, and primer and probe concentrations were adjusted to 180 nM and 80 nM, respectively.

Example 3

Comparison of Direct PCR and Fluorogenic Real Time PCR Assays

Analyses were first performed by direct PCR using universal 18S rRNA primers or T. gondii ITS1 primers (Table 1). Approximately 150 ng of DNA from each sample was tested. Samples included pig, mouse, N. caninum, H. hammondi, E. acervulina, E. tenella, S. ovicanis, S. muris, C. parvum, T. gondii and control (no DNA). The PCR products were electrophoresed in a 1.5% agarose gel, stained with ethidium bromide and the image photographed (FIGS. 1A and 1B).

Additionally, the fluorogenic real time PCR assay was performed where 100 ng of T. gondii DNA was analyzed instead or 150 ng as used for all other samples because of the thick band observed for T. gondii DNA in the previous PCR. Samples were assayed on an ABI PRISM® 7700 Sequence Detector (Applied Biosystems, supra) and analyzed using the SDS version 1.7 software (FIG. 1C). Reporter dye fluorescence is plotted on the y-axis (λ Rn) and cycle number on the x-axis. The amplification plot shows test results from T. gondii DNA through 50 cycles. Other samples are below the treshold line and are indicated in bold.

Example 4

Sources of T. gondii

Three strains of T. gondii representing all three known genotypes (RH, genotype I; Me49, genotype II; BEG, genotype III) were used to infect animals in this study (Howe and Sibley. 1995. J. Infect. Dis. vol. 172, pp. 1561–1566). All three infective stages of T. gondii, i.e. tachyzoites, bradyzoites and oocysts, were used for the extraction of genomic DNA or to infect animals (Dubey and Beattie. 1988. Toxoplasmosis of Animals and Man. CRC Press, Boca Raton, Fla.). To determine the minimum infective dose (i.e. 1 parasite), ten-fold dilutions of tachyzoites, bradyzoites and oocysts were bioassayed in mice.

Tachyzoites were obtained from peritoneal lavage of mice injected intraperitoneally 3–5 days earlier with RH strain tachyzoites. The peritoneal fluid was passed through a 3-µm filter (Nucleopore, Pall Gelman, Ann Arbor, Mich.) to remove host cells. Tachyzoites were pelleted by centrifugation at 1,180×g for 10 min and the number of parasites counted with a hemocytometer. T. gondii genomic DNA was extracted from approximately $10^8$ tachyzoites after overnight incubation with DNA digestion buffer (SDS 0.5%, 25 mM EDTA, 100 mM NaCl, 20 mM Tris-HCl pH 8.0, proteinase I 0.1 mg/ml final concentration). Digested parasites were extracted by phenol:chloroform:isoamyl alcohol (25:24:1) and the DNA precipitated in 0.3 M sodium acetate (final concentration) with 2.5 vol of ethanol 100%. DNA pellets were solubilized in TE buffer (10 mM Tris-HCl, 1 mM EDTA) and stored at −20° C. The DNA concentration was estimated by spectrophotometric absorbance at 260 nm.

Oocysts were obtained from feces of cats fed tissue cysts of the VEG strain, as described by Dubey et al., 1996 (supra). Bradyzoites were collected from the brains of female Swiss-Webster mice chronically infected with the VEG strain (Dubey and Beattie, supra). All brains were homogenized and tissue cysts isolated by centrifugation through an isotonic Percoll gradient. Bradyzoites were released from tissue cysts by short incubation with pepsin-HCl solution at room temperature, neutralized with sodium bicarbonate and counted with hemocytometer (Dubey, J. P. 2000. J. Parasitol. In Press). Ten-fold dilutions were prepared in PBS, pH 7.2, and added to 1 g of muscle (biceps femoral) samples from T. gondii-free pigs. The spiked tissue samples were pepsin-HCl digested and treated for DNA extraction as described supra at a ratio of 1.2 ml/0.1 g of tissue. DNA (500 ng total input) from each muscle sample was analyzed in duplicate, on 4 different days.

Example 5

Verification of Fluorogenic Real Time PCR Specificity

A panel of DNA samples from the related protozoa N. caninum, H. hammondi, Eimeria acervulina, E. tenella, Cryptosporidium parvum, Sarcocystis muris, S. ovicanis as well as T. gondii was tested for primer specificity. Amplification of the 18S rRNA gene for each sample was performed with universal primers (Table 1) to normalize the quality and quantity of DNA between samples. DNA samples from muscle and brain of host animals (pig and mouse) were similarly tested. Approximately 150 ng of each parasite DNA was evaluated with 18S rRNA universal primers and with the T. gondii ITS1 primers. Results are shown in FIG. 1.

Example 6

Sensitivity of Fluorogenic Real Time PCR Assay

Dilutions of T. gondii DNA containing 100 ng, 10 ng, 1 ng, 100 pg, 10 pg, 1 pg, 0.1 pg, 0.01 pg and control (no template) were assayed. Results are shown in FIG. 2 where the assay threshold limit is represented as a bold line and positive signals ($C_T$ values) for the dilutions are shown in panel A. The PCR products were electrophoresed in 1.5% agarose gel, stained with ethidium bromide and the image photographed, as shown in panel B. Mean $C_T$ values from 8 replicates, tested on different days, were plotted against the *T. gondii* DNA inputs (log pg) and are shown in panel C.

Example 7

Analysis of Tissues from *T. gondii*-Infected Animals

*T. gondii* DNA was extracted from tissue cysts obtained from chronically infected mice. Five Swiss-Webster mice were injected subcutaneously (SC) with 200 counted bradyzoites of the VEG strain. Six weeks later, animals were bled, and serology was performed using a modified agglutination test (MAT) at a 1:50 screening dilution of the serum (Desmont and Remington, supra). Animals were subsequently killed, the whole brains collected and smears made to verify tissue cysts. Remaining brain tissue was directly processed with DNA digestion buffer, without treatment with pepsin-HCl. DNA was extracted as described supra and stored at −20° C. for future use. Brain tissue from 4 mice infected with the Me49 *T. gondii* strain were also included in this experiment and processed in a manner similar to those from VEG-infected mice.

Five seronegative (MAT titers <1:25) NIH miniature pigs (age ~6 months) were orally inoculated with 500 oocysts of the VEG strain, and located in an isolated building, as previously described (Dubey et al., 1996., supra). Two seronegative pigs were kept as negative controls. Thirty-five to 42 days after the infection, all pigs were killed, and brain and tongue samples were collected for bioassays and blood samples for serology. Tongue and brain were selected for parasite burden because these tissues are the most heavily parasitized among all pig tissues tested (Dubey and Beattie, supra; Dubey et al., 1996, supra).

For the fluorogenic real time pig tissue analyses, approximately 50 g of brain or tongue from each pig, or 1 g of *T. gondii* bradyzoite-spiked muscle samples, were homogenized in a blender with 5 volumes of sterile saline solution. Samples were then digested with an equal volume of pre-warmed (37° C.) pepsin-HCl (1.4 mg/ml pepsin, 10 mg/ml NaCl, 0.1 N HCl) for 1 h at 37° C. in a shaking water bath. The mixture was neutralized by 2 washes with 0.1 M Tris buffer pH 8.0 and centrifuged for 10 min at 1,180×g. The resulting pellet was digested overnight at 55° C. with DNA digestion buffer. DNA was extracted as described above and stored at −20° C.

Example 8

Statistical Analyses

In order to determine the variability of the assay, precision intra-assay and inter-assay (repeatability) was measured. Ten replicates of three different *T. gondii* DNA concentrations (10 pg, 100 pg and 1 ng) and a *T. gondii*-spiked muscle sample, randomly distributed through the 96-well format of the thermal cycler, were simultaneously tested. The repeatability of the test (precision between runs) was assessed using the previous *T. gondii* DNA concentration, testing 4 replicates of each, on 5 different days. Variability is shown as the mean±ISD in the graphs and reported as coefficient of variation (CV). Statistical analyses were carried out using Microsoft Excel (Redmond, Wash.).

We claim:

1. An oligonucleotide primer selected from the group consisting of sequence 5'-GATTTGCATTCAAGAAGCGTGATAGTAT-3' (SEQ ID NO: 1) and sequence 5'-AGTTTAGGAAGCAATCTGAAAGCACATC-3' (SEQ ID NO: 2).

2. An oligonucleotide primer consisting of sequence 5'-GATTTGCATTCAAGAAGCGTGATAGTAT-3' (SEQ ID NO: 1).

3. The primer of claim 2, wherein said primer comprises a detectable label.

4. The primer of claim 3, wherein said detectable label is selected from the group consisting of radioactive, calorimetric, fluorometric, luminescent and organic labels.

5. An oligonucleotide primer consisting of sequence 5'-AGTTTAGGAAGCAATCTGAAAGCACATC-3' (SEQ ID NO: 2).

6. The primer of claim 5, wherein said primer comprises a detectable label.

7. The primer of claim 6, wherein said detectable label is selected from the group consisting of radioactive, calorimetric, fluorometric, luminescent and organic labels.

8. An oligonucleotide primer pair comprising sequence 5'-GATTTGCATTCAAGAAGCGTGATAGTAT-3' (SEQ ID NO: 1) and sequence 5'-AGTTTAGGAAGCAATCTGAAAGCACATC-3' (SEQ ID NO: 2).

9. The primer pair of claim 8, where in at least one primer comprises a detectable label.

10. The primer pair of claim 9, wherein said detectable label is selected from the group consisting of radioactive, calorimetric, fluorometric, luminescent and organic labels.

11. An oligonucleotide probe effective for the specific detection of amplification products of DNA from *Toxoplasma gondii* consisting of sequence 5'-CTGCGCTGCTTCCAATATTGG-3' (SEQ ID NO: 3).

12. The probe of claim 11, wherein said probe comprises a detectable label.

13. The probe of claim 12, wherein said detectable label is selected from the group consisting of radioactive, calorimetric, fluorometric, luminescent and organic labels.

14. The probe of claim 11, wherein said probe is detectably labeled with a fluorescent reporter substituent at the 5' end and a fluorescence quencher substituent at the 3' end.

15. A method of detecting *Toxoplasma godnii* by a polymerase chain reaction assay, said method comprising a) providing a test sample suspected of containing *Toxoplasma godnii* DNA, b) amplifying said DNA with oligonucleotide primers 5'-GATTTGCATTCAAGAAGCGTGATAGTAT-3' (SEQ ID NO: 1) and 5'-AGTTTAGGAAGCAATCTGAAAGCACATC-3' (SEQ ID NO: 2) and c) detecting the presence of amplified DNA as an indication of the presence of *Toxoplasma godnii* in the test sample.

16. The method of claim 15, wherein at least one primer comprises a detectable label.

17. The method of claim 16, wherein said detectable label is selected from the group consisting of radioactive, calorimetric, fluorometric, luminescent and organic labels.

18. The method of claim 15, wherein said detecting step is carried out with an oligonucleotide probe having sequence 5'-CTGCGCTGCTTCCAATATTGG-3' (SEQ ID NO: 3), and wherein said probe comprises a detectable label.

19. The method of claim 18, wherein said detectable label is selected from the group consisting of radioactive, calorimetric, fluorometric, luminescent and organic labels.

20. The method of claim 15, wherein said detecting step is carried out by chemical staining.

21. The method of claim 15, wherein said detecting step is carried out by Southern or dot blot hybridization.

22. The method of claim 18, wherein said detectable label comprises a fluorescent reporter molecule and a fluorescence quencher molecule.

* * * * *